(12) United States Patent
Hill

(10) Patent No.: US 7,125,518 B2
(45) Date of Patent: Oct. 24, 2006

(54) AEROSOL PARTICLE ANALYZER FOR MEASURING THE AMOUNT OF ANALYTE IN AIRBORNE PARTICLES

(75) Inventor: Steven Clyde Hill, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 179 days.

(21) Appl. No.: 10/708,191

(22) Filed: Feb. 14, 2004

(65) Prior Publication Data

US 2005/0179893 A1    Aug. 18, 2005

(51) Int. Cl.
  *B32B 5/02* (2006.01)
  *B32B 27/04* (2006.01)
  *B32B 27/12* (2006.01)
  *G01N 30/96* (2006.01)
  *C12M 1/34* (2006.01)

(52) U.S. Cl. ............. 422/88; 422/83; 422/82.05; 422/82.08; 435/7.1; 435/283.1; 435/288.7; 436/35; 436/36; 436/149; 436/153; 436/172; 436/181; 356/36; 356/37; 356/300; 356/318; 356/335; 250/281; 250/282; 250/283; 250/288; 250/299

(58) Field of Classification Search ............. 436/35, 436/36, 149, 153, 172, 181; 422/83, 88, 422/82.05, 82.08; 435/7.1, 283.1–283.2, 435/288.7; 356/36, 37, 300, 318, 335; 250/281–283, 250/288, 299
See application file for complete search history.

(56) References Cited

U.S. PATENT DOCUMENTS 5,532,140 A * 7/1996 Arnold et al. ............. 435/34
2005/0214168 A1* 9/2005 Lin et al. ................. 422/83

OTHER PUBLICATIONS

U.S. Appl. No. 11/126,515, filed May 2005, Hill et al.*
Lamb, Dennis; Moyle, Alfred M.; and Brune, William H. "The Environmental Control of Individual Aqueous Particles in a Cubic Electrodynamic Levitation System." Aerosol Science and Technology. vol. 24: 263-278 (1996).*

* cited by examiner

*Primary Examiner*—Long V. Le
*Assistant Examiner*—Jacqueline A DiRamio
(74) *Attorney, Agent, or Firm*—A. David Spevack; Guy M. Miller; Stephen M. Bloor

(57) ABSTRACT

Aerosol particle analyzer (APA) for measuring the amount of analyte in airborne particle is described. The APA uses an analysis liquid. When this analysis liquid is mixed with the particles, an optical property of the analysis liquid (CDAL) varies according to the amount of the analyte in the particles. A charged droplet of the analysis liquid is levitated. Airborne particles are drawn into the instrument and given a charge that is opposite that of the CDAL, and made to flow near the CDAL so that electrostatic forces greatly increase the probability that the CDAL and charged particles will combine. Then the CDAL is ejected into a horizontally oriented linear quadrupole that is in an airtight container, except for a small orifice to let the CDAL enter. The CDAL is levitated in a high humidity environment so that it evaporates slowly, so that there is time for the reaction between the analyte, if any, and the CDAL can take place, and so that the optical property, typically fluorescence, can be measured. The amount of the analyte in the particle is determined from the measured fluorescence or other optical property.

30 Claims, 14 Drawing Sheets

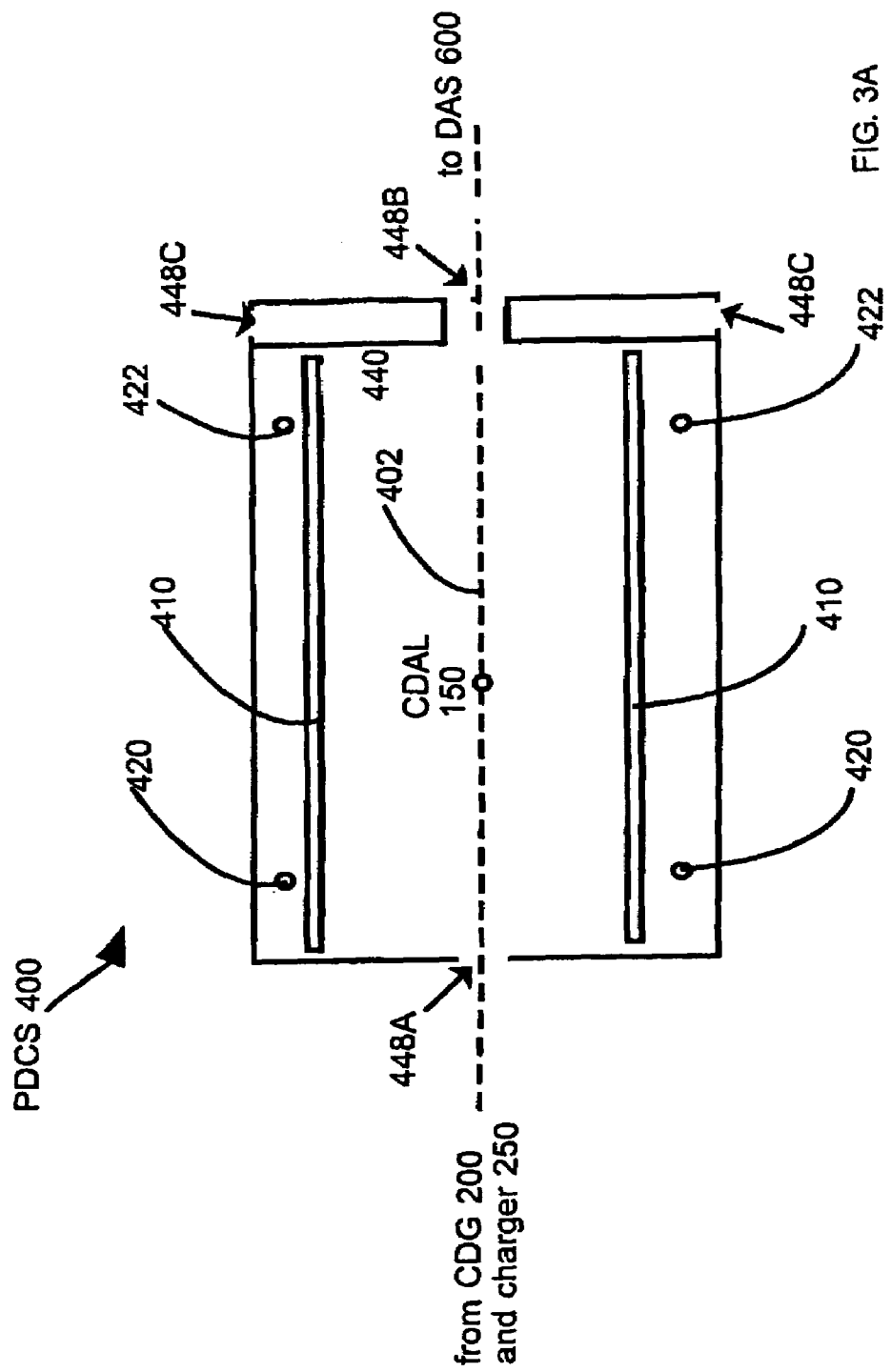

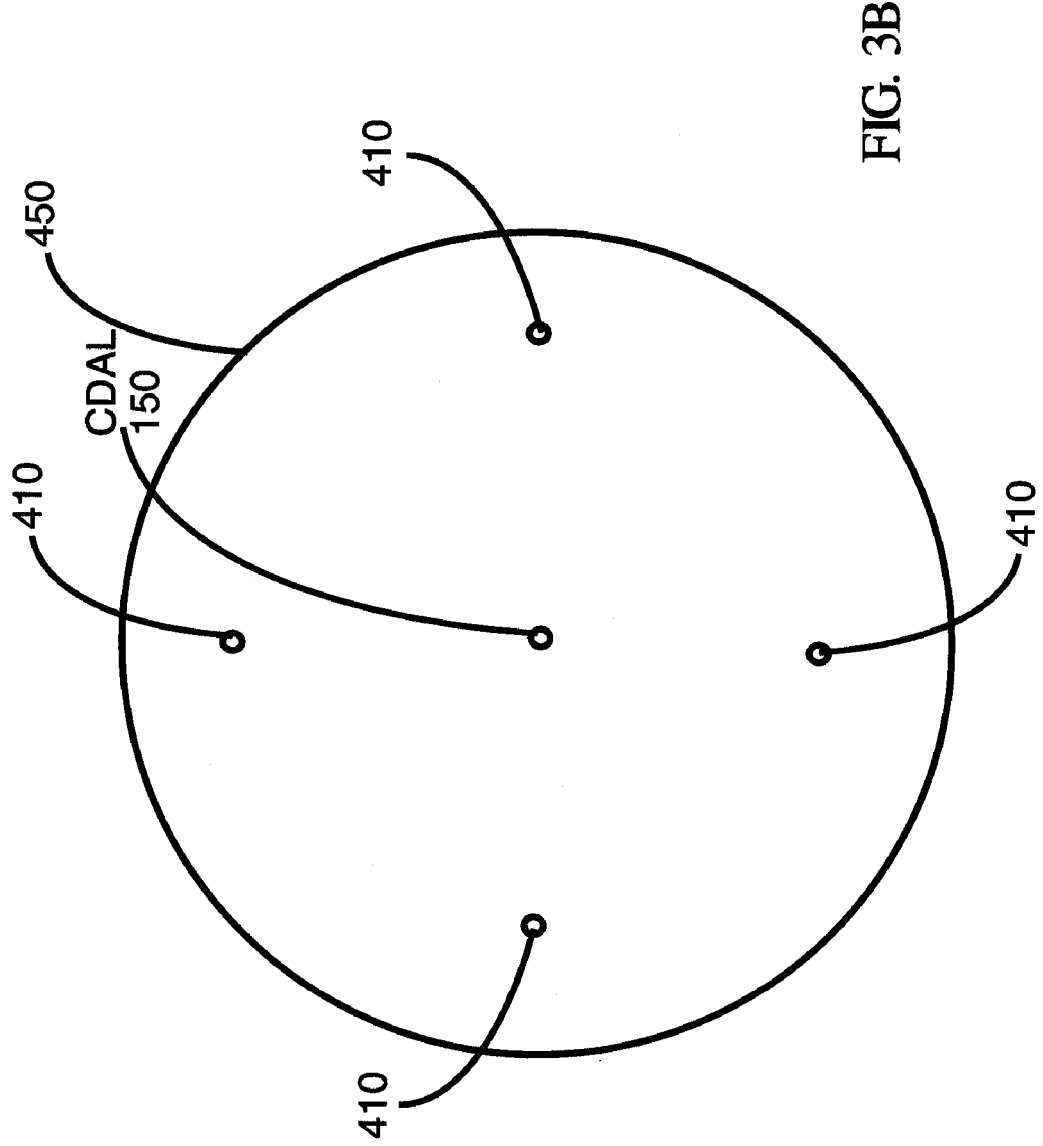

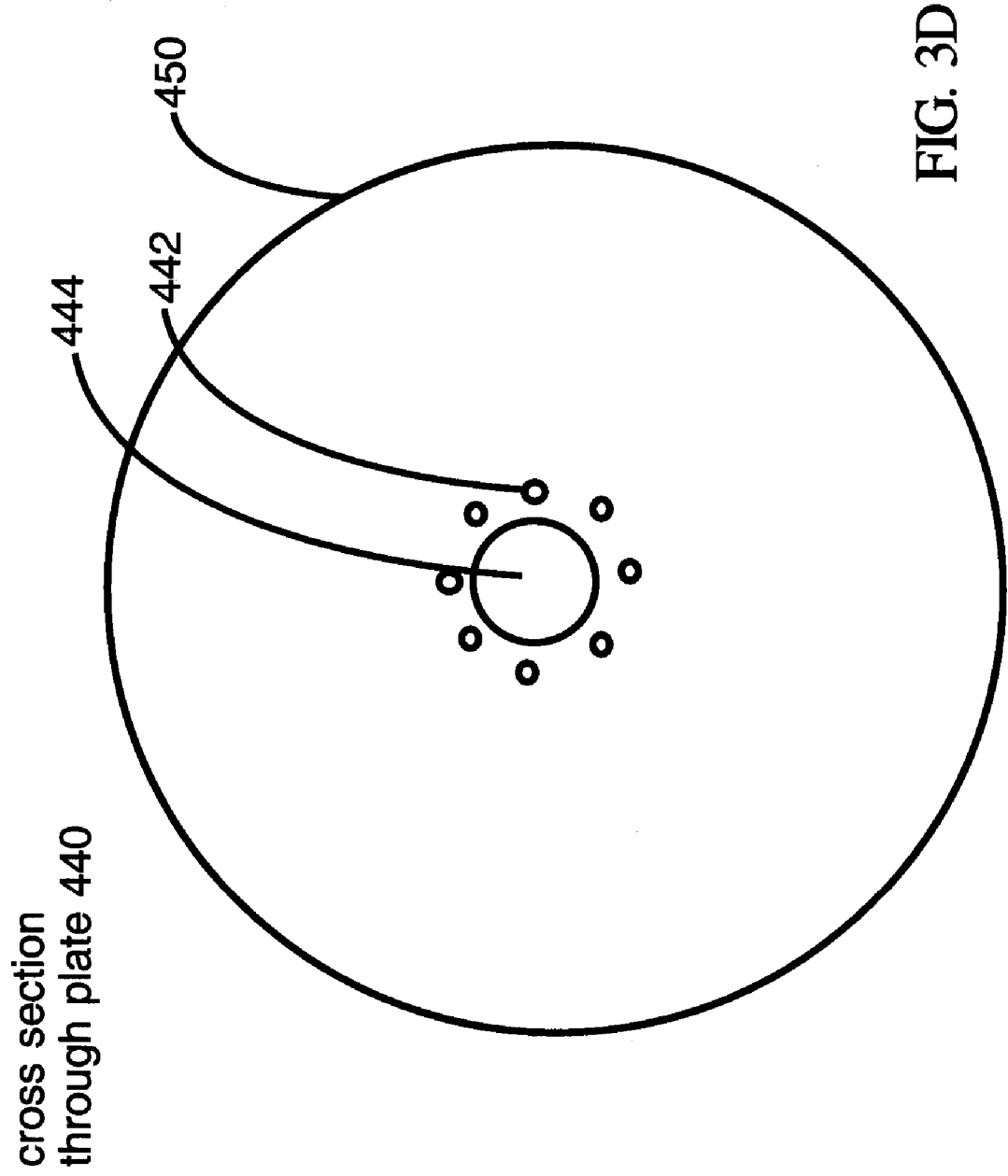

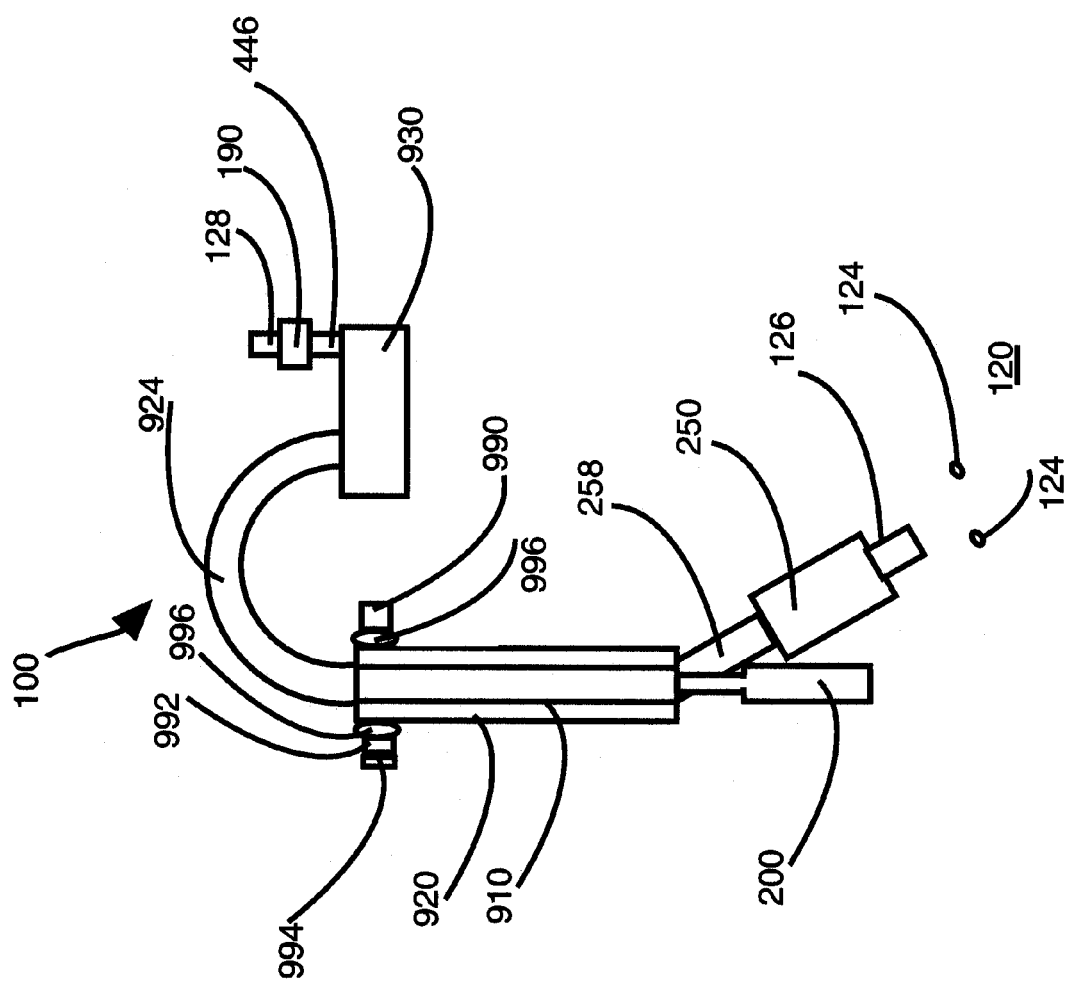

Figure 1A:
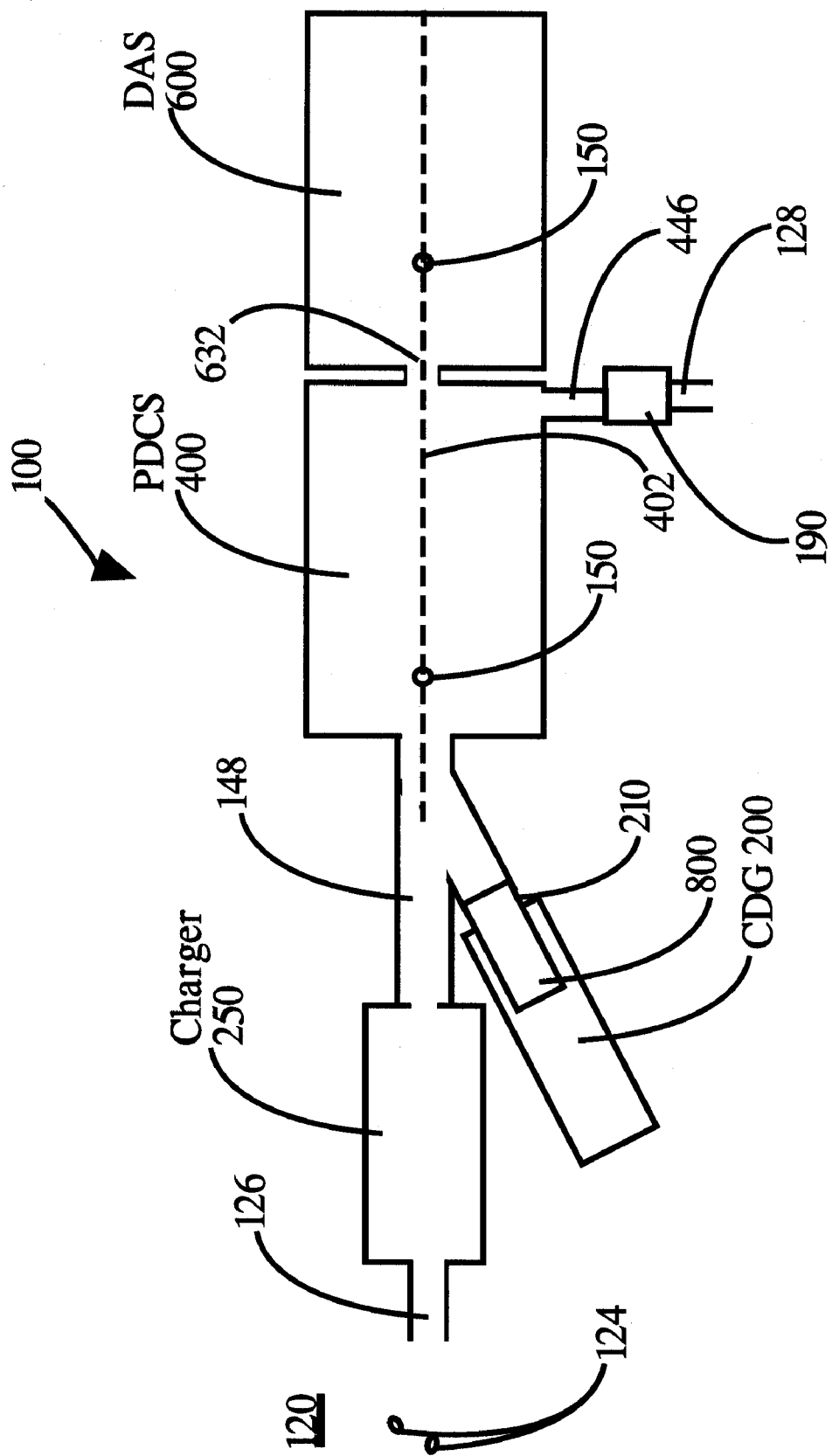

AEROSOL PARTICLE ANALYZER FOR MEASURING THE AMOUNT OF ANALYTE IN AIRBORNE PARTICLES

BACKGROUND OF INVENTION

1. Field of the Invention

This invention pertains generally to chemical analytical and immunological testing, and particularly to processes wherein samples are analyzed by using self-operated mechanisms or devices, and more particularly to processes wherein a continuously flowing stream of a sample or carrier fluid is formed and flows into and through analysis wherein the continuously flowing stream is segmented by alternately injecting a sample, reagent or any number of fluids into a common flow path.

2. Description of the Related Art

Recent events have highlighted the need for devices that can quickly ascertain and identify the presence of harmful materials in airborne particles. There is also a more general need, beyond the biological-warfare (BW) agent detection problem, for improved methods for measuring analytes in airborne particles. For example, airborne infectious agents (bacteria, viruses) transmit many diseases of humans, other animals, or plants. Some airborne proteins and pollens cause allergies. Improved methods for characterizing aerosols would be useful for understanding atmospheric chemistry, including the sources, chemical reactions, and fates of atmospheric particles.

Here, "airborne particle" refers to both the solid particles and liquid droplets in an air sample. The analyte is the specific molecule, microorganism, or virus to be identified. For example, for biological warfare agents that are protein toxins, e.g., ricin, the toxin itself is the analyte. For BW agents that are bacteria or viruses, the analyte can be a molecule that is specific to the bacteria or virus to be detected, e.g., a protein or a DNA or RNA sequence. In this case the amount of the analyte is measured; if this amount is significantly above a noise threshold, the presence of the BW agent is inferred. For BW agents that are bacteria or viruses, the analyte can be the bacteria or virus itself.

Key objectives for some types of instruments needed for detecting BW-agents or other analytes in airborne particles are:

(a) Sensitivity. An instrument should be able to measure and identify small amounts of a BW-analyte in the particles in an air sample, because small amounts of BW agents may be lethal.

(b) Specificity. An instrument should have a very low rate of false positives, i.e., reporting a BW-analyte when it is not in the air sample.

(c) Rapid response. An instrument should have no more than a short delay between the time a BW aerosol enters the instrument and the time the instrument indicates that a BW-analyte has been identified. The sooner people know they are under attack, the sooner they can take protective measures if available, and/or try to leave the region of exposure, and/or seek medical treatment. Also, with a sufficiently rapid alert some people can avoid exposure altogether.

(d) Continuous operation. An instrument should be able to run essentially continuously for days or weeks at a time. It should run continuously because BW aerosols could appear at any time. Presently, "trigger" instruments, which run continuously but cannot identify BW-agents, are used to tell when to turn on instruments that can identify agents. If there were some "trigger" instrument that was adequate for telling when to turn on an identifier, there would be no need for an identifier. But it is difficult to imagine that any of the reagentless techniques being investigated or suggested for trigger instruments would be able to identify specific BW agents in cases where these BW agents comprise a small fraction of the total particles in a complex mixture of airborne particles.

(e) Little need for consumables. An instrument should not require large amounts of consumables (e.g., liquids, antibodies, microscope slides, filters). The more consumables required, the fewer BW-aerosol-detection instruments that can be maintained in continuous operation.

(f) Little need for operator time. If more operator time is required, fewer BW-aerosol-detection instruments can be maintained in continuous operation.

(g) Be able to separate and store particles for further analysis. It is desirable to confirm the detection of analyte using complementary techniques which may be much less rapid.

Investigators have worked for years to develop instruments and methods that are useful for detecting airborne BW agents. Samples can be collected from air using a variety of different collectors, and the collected samples can be subjected to many different types of microbiological and biochemical analyses. Therefore, the number of possible approaches is very large. Because of the importance of the problem, progress is being made, e.g., improved recognition molecules such as antibodies and aptamers for BW agents are being developed; more rapid methods of extracting DNA and RNA from spores are being explored; methods for detecting very small amounts of analytes or very small amounts of antigen-antibody reactions are being improved and new methods are being developed; improved methods of concentrating airborne particles, and collecting them from air are being developed; and instrumentation is being developed to perform the analysis in an automated fashion, for example, an automated flow cytometer has been developed for BW-agent detection.

None of these methods adequately satisfy the objectives stated above simultaneously. Some reasons for these objectives not being met simultaneously are as follows. Objectives (a) and (b) require sensitivity and specificity. To measure the amount of an analyte that is a BW agent or is indicative of a BW agent in a complex sample (collected from air or otherwise), requires the sample to be mixed with one or more liquids, termed here, "analysis liquids." At least one of these liquids contains sensor molecules, also termed recognition molecules, that selectively bind to or interacts with the analyte. Example recognition molecules are antibodies and aptamers. Aptamers are DNA or RNA molecules that are selected for their ability to bind to the analyte. As a result of this binding of the recognition molecule to the analyte, some measurable property, e.g., fluorescence, must change according to the amount of analyte in the sample. That property is measured and the amount of analyte is inferred. Objectives (c) and (d) require continuous operation for days or weeks, and therefore continuous expenditure of consumables. Therefore, because of objective (e) limiting consumables, each measurement must require only a very small amount of consumables. In addition to the consumables used in analyzing the sample, consumables are typically expended in collecting particles from the air to be analyzed. If the particles are collected on filters or impacted on a surface, the filter or surface is a consumable unless it is cleaned, in which case whatever is used to clean it may be consumed. In typical analysis procedures for biochemical analytes in airborne particles, the airborne particles are collected into a liquid, which tends to evaporate as the sample is collected, especially if the air sample is warm and dry.

The objectives of sensitivity and specificity, suggest choosing as analytes specific DNA or RNA sequences, and this approach may be applicable for some analytes. However, objective (c) for a rapid response makes this approach not feasible for spores because 10's of minutes are required for the DNA from a spore to be extracted, amplified and detected. Also, this approach is not applicable to BW agents that do not contain DNA or RNA, such as protein toxins.

Arnold, Hendrie and Bronk (U.S. Pat. No. 5,532,140, Method and Apparatus for Suspending Microparticles, herein incorporated by reference) described a linear quadrupole (LC) with rings to control particle motion. They describe how the positions of the charged particles can be controlled by moving storage rings that encircle the LQ, and they describe how oppositely charged particles can be combined by moving them toward each other by moving the storage rings. Although the Background and the Summary of the Invention mention the problem of characterizing atmospheric, and biological warfare agent aerosols, there is nothing in the detailed description of the invention that suggests colliding an atmospheric aerosol particle with a droplet. The two droplets that collide are each generated with a piezoelectric droplet generator and a charging plate, which combination I term a charged-droplet generator (CDG). Because the two charged droplets are each generated with a CDG, one has the impression that the atmospheric particles would first be collected into a liquid, and the droplets would be generated from this liquid. That approach is valid, but would require more liquid for each particle than if each atmospheric particle of interest is collided with a single droplet, and it is susceptible to particles sticking to surfaces, etc. Arnold and coworkers (A. F. Izmailov, A. S. Myerson, S. Arnold, "A statistical understanding of nucleation," J. Crystal Growth, 196, 234–242 (1999), especially FIG. 1 and pages 238 and 240, both herein incorporated by reference) further stated that their experiments show they "can simultaneously levitate in excess of 100 identical microdroplet particles within the same LQELT. These particles produce a periodic one-dimensional lattice." M. D. Barnes, N. Lermer, C.-Y. Kung, W. B. Whitten, J. M. Ramsey, S. C. Hill, "Real-time observation of single-molecule fluorescence in microdroplet streams," Optics Letters, 22, 1265–1267 (1997), incorporated herein by reference, showed that single fluorescence molecules in droplets can be detected. The droplets are generated with a droplet generator and a charging ring, a combination that comprises a charged droplet generator (CDG), and are then confined by a LQ to the axis of the LQ. Laser induced fluorescence from the single molecule, is detected as the droplet flows through a laser beam that is perpendicular to and passes through the LQ axis. In other experiments, particles as small as 1 micrometer have been shown to have trajectories that remain very near the LQ axis.

Individual droplets can be levitated and their reactions with gases or particles can be monitored. See E. James Davis and Gustav Schwieger, The Airborne Microparticle, Its Physics, Chemistry and Transport Phenomena (Springer-Verlag, Berlin, 2002), especially pp. 69–116 (with references) for electrodynamic levitators, and pp. 682–714 (with references) for measurements of chemical reactions in falling or levitated droplets. A commonly used electrodynamic levitation apparatus is termed the electrodynamic balance (EDB). It confines particles in three dimensions. C. L. Aardahl, J. F. Widmann, and E. J. Davis, in "Raman Analysis of Chemical Reactions Resulting from the Collision of Micrometer-Sized Particles," Applied Spectroscopy, 52, 47–53 showed that two particles levitated in an EDB could be combined and the reaction between them monitored using Raman scattering.

SUMMARY OF INVENTION

In consideration of the problems detailed above and the limitations in the partial solutions thereto, an object of the present invention is to provide an improved aerosol particle analyzer (APA) for measuring the amount of analyte in airborne particles. In this invention the term "particles" includes both solid and liquid particles.

Another object of the present invention is to provide an APA that is sensitive to a small number of particles that contain the analyte in a large volume of air;

Yet another object of the present invention is to provide an APA that is specific for the analyte;

Yet a further object of the present invention is to provide an APA that has a rapid response, with no more than a short delay between the time the analyte aerosol enters the instrument and the time the instrument indicates that an analyte has been identified.

Yet another object of the present invention is to provide an APA that can run continuously.

Yet another object of the present invention is to provide an APA that has a low requirement for consumables.

Yet another object of the present invention is to provide an APA that has little need for operator time.

In order to attain the objectives described above, according to an aspect of the present invention, there is provided an aerosol particle analyzer for measuring the amount of an analyte in airborne particles in a gas such as the atmosphere. The main parts of this airborne particle analyzer are as follows.

(i) an analysis liquid that has the following property: when the analysis liquid is mixed with particles, the fluorescence of the analysis liquid varies according to the amount of the analyte in the particles, so that the amount of analyte can be determined from measurements of the fluorescence. No wash steps or separation is allowed, that is, the analysis liquid used in this present invention must be suitable for a homogeneous assay. To achieve the objective of specificity, the analysis liquid typically requires molecules, such as aptamers, antibodies, nucleic acids, or phage-displayed epitopes, that are specific for the analyte. To help achieve the objective of sensitivity, the analysis liquid typically uses a reporter molecule such as a fluorophore that can be detected even in very low amounts.

(ii) A charged-droplet generator ejects a charged-droplet of the analysis liquid (CDAL) when signaled to do so. Because the CDAL is typically less than micrometers in diameter, it is possible to eject CDAL at a rate of a few per second and still satisfy the objective of using only a small amount of consumables.

(iii) A charger that imparts an electrical charge to particles drawn through it, where the sign of this charge is opposite that of the charged droplets of the analysis liquid, so that the charged particles will be attracted to the CDAL and combine with them. Charging these particles so that they combine more efficiently with the CDAL helps reduce the requirement for consumables because each CDAL collects more particles from the gas.

(iv) A particle-droplet-collision subsystem (PDCS) that has an electrodynamic levitator that levitates the charged droplet of the analysis liquid while the charged particles in the gas are drawn past it by a vacuum pump, so that many of the charged particles come close enough to the CDAL to be electrostatically attracted to it and to collide and combine with it. The PDCS also expels the CDAL in a desired direction via the PDCS-CDAL output when signaled to do so. The PDCS provides a way for particles to be collected from the air sample and to be mixed with the analysis liquid very efficiently and without coming into contact with surfaces that may become contaminated and require cleaning or replacement, and by doing so satisfies the objectives of using only a small amount of consumables, and because the particles and analysis liquid do not come into contact with surfaces, there is less chance for interference and this low probability of interference helps contribute to the high sensitivity of the APA.

(v) A vacuum pump connected to the PDCS vacuum connection that draws the gas and particles into the charger gas input and through the charger and then on into the PDCS.

(vi) A droplet analysis subsystem (DAS) that accepts the CDAL ejected by the PDCS, and levitates these CDAL for the time needed for the analyte to react with the analysis liquid and for the fluorescence to change if analyte is present, and for the time required for measurement of the fluorescence. The DAS is substantially airtight, except for the hole through which the CDAL is injected, so that water vapor leaks relatively slowly from the DAS so that the humidity in the DAS remains high, so that the CDAL evaporates slowly, so that there is sufficient time for the reaction between the analyte and the analysis liquid to take place and for the fluorescence to be measured, so that the amount of analyte in the particles can be determined.

Other components used in some embodiments of the APA are:

(i) A linear quadrupole (LQ) aligned vertically. The gas, charged particles, and CDAL are drawn into this LQ from the bottom and are drawn upward through it by the vacuum in the PDCS. The CDAL is larger and heavier, and the particles flow past it with a velocity near that of the gas, while the CDAL is drawn upward but at a slower velocity. As the particles and CDAL move upward, the LQ pushes them toward the LQ axis, and the particles and CDAL are attracted, because they are charged oppositely, and they collide and combine. This LQ can make the APA more sensitive because a higher fraction of the particles combine with the CDAL and are analyzed, and, at least at low concentrations of particles, it can reduce the need for consumables because with more efficient collisions between particles and CDAL, a smaller amount of the analysis liquid is required.

(ii) An aerosol particle concentrator that concentrates particles in the air before they enter the charger. It can greatly increase the sensitivity of the APA.

(iii) An aerosol particle counter (APC) that measures the numbers of particles in different size ranges. This APC can be especially useful in cases where it is more probably that nonspecific reactions will occur between the analysis liquid and other molecules that are not the analyte. If such reactions result in changes in fluorescence that appear like those that occur with the analyte, then the sensitivity is reduced, or the false positive rate is increased. The APA must be calibrated so that the mass of the particles that combine with each CDAL can be determined from APC measurements of the particle size and number. Then this measured mass of the particles that combined with the CDAL can be used with the fluorescence measurement of the CDAL to give the analyte per mass of particles that combined with the CDAL. If a very small fluorescence signal is measured for a small mass of particles, this is far more likely to be analyte than if the same small amount of fluorescence were measured for a relatively large mass of particles.

A novel feature of an embodiment of the APA described in the present invention is the ability to: (a) collect charged particles from the air efficiently into a very small volume of the analysis liquid, i.e., into a microdroplet, while the air is flowing somewhat rapidly past the CDAL so that a large number of particles can collide with the CDAL, and, (b) levitate the droplet for the time required for the analyte to react with the analysis liquid and for the change in fluorescence to be detected, because the CDAL is injected into a DAS chamber where the humidity is kept high because the DAS is airtight, except for a small orifice where the CDAL enter, and because CDAL are continually being injected into the DAS, and as they evaporate slowly, they help keep the humidity high.

The aforementioned features, objects, and advantages of this method over the prior art will become apparent to those skilled in the art from the following detailed description and accompanying drawings.

BRIEF DESCRIPTION OF DRAWINGS

In the drawings:

FIGS. 1A, 1B, and 1C are schematics drawings illustrating the APA;

FIG. 2. illustrates schematically an embodiment of the reaction that takes place in the charged droplet of the analysis liquid (CDAL) when analyte is present in a particle that collided with the droplet;

FIG. 3A–F illustrate schematically the particle-droplet collision subsystem;

FIGS. 4A and 4B illustrates schematically the droplet analysis subsystem (DAS);

FIG. 5 illustrates schematically another embodiment of the APA, one that uses a vertically-oriented linear quadrupole and does not include a DAS; and FIG. 6 illustrates schematically another embodiment of the APA, one that does not include a DAS.

DETAILED DESCRIPTION

Referring to FIG. 1A-FIG. 1C & FIG. 2 an aerosol particle analyzer (APA) 100 is immersed in a gas such as the atmosphere, having particles therein. Generally, the particles include many types of particles 124, some of which may contain no analyte 80, and some of which may contain some amount of the analyte 80. The particles 124 may be liquid, solid, or a mixture of liquid and solid.

An analysis liquid 800 is in a reservoir 210 in the droplet generator 200. The analysis liquid 800 is chosen to have the following property: when the analysis liquid 800 is mixed with particles 124, the fluorescence of the analysis liquid 800 varies according to the amount of the analyte 80 in the particles 124, so that the amount of analyte can be determined from measurements of the fluorescence. No wash steps or separation is allowed, that is, the analysis liquid 800 used in this present invention must be suitable for a homogeneous assay.

The measurement of the analyte 80 in the particles 124 is accomplished as follows. The pump draws gas 120 and particles 124 into the APA 100 through an induction port 126 then through a charger 250 that imparts a negative charge to the particles 124, then through the particle-droplet-collision subsystem (PDCS) 400, and then exhausts at least the gas 120 out of an eduction port. The charged-droplet generator (CDG) 200 ejects a charged-droplet-of-the-analysis-liquid CDAL 150 into the flow of gas 120 and particles 124 being drawn into the (PDCS) 400, with a direction and velocity such that it enters PDCS 400 substantially along the PDCS axis 402 and then is levitated. A Y-connector tube 148 connects the charger 250 to the PDCS 400 and also connects the CDG 200 to the PDCS 400 in a way that allows the CDAL 150 ejected from the CDG 200 to enter the PDCS 400 along the PDCS axis 402. As the particles flow through the PDCS 400, at least some of the particles 124 collide with the CDAL 150 and combine with it. The polarity of the charge imparted to the particles 124 by the charger 250 is the opposite of the polarity of the CDAL 150, so that electrostatic forces increase the number of the particles 124 that combine with the CDAL 150. More than one particle 124 may combine with the CDAL 150. The charge on the CDAL 150 remains substantially the same as that of the CDAL 150 ejected from the CDG 200 because the magnitude of the charge on the particles 124 that combine with the CDAL 150 is substantially smaller than the charge of the CDAL 150. If one or more of the particle(s) 124 that mix with to CDAL 150 contain some analyte 80, the fluorescence of the CDAL 150 begins to change in accordance with the amount of the analyte 80. After a time, the CDAL 150 is ejected by the PDCS 400, and moves into the droplet analysis system DAS 600. In the DAS 600 the CDAL 150 is levitated for time sufficient for the analyte 80 to react with the analysis liquid to generate fluorescence, and then the fluorescence of the CDAL 150 is measured. The amount of the analyte 80 in the particles that collided with the CDAL 150 is determined from this measured fluorescence. When the CDAL 150 is ejected, the CDG 200 injects another CDAL 150 into the PDCS 400. A computer, controller, voltage sources and electronics subsystem (CCVSES) controls the timing of the generation of the CDAL 150, the motion of the CDAL 150, and the measurement of the fluorescence and the determination of the amount of analyte from that measured fluorescence.

By using only a small amount of the analysis liquid 800, i.e., the amount of analysis liquid 800 in a CDAL 150, for each measurement, the APA 100 satisfies one objective of the APA 100. By keeping the CDAL 150 levitated from the time of generation of the CDAL 150 to the time of measurement of the fluorescence, the APA 100 avoids contact of the CDAL 150 with any surface, and thereby eliminates cross contamination and reduces the need for replacing expendable items, thereby satisfying another objective of the APA 100. By separating the PDCS 400, in which the gas 120 flowing past the CDAL 150 may have a very low humidity, from the DAS 600, which is airtight except for the inlet orifice 632 through which CDAL 150 from the PDCS 400 enters, and so the humidity in the DAS 600 can be kept high enough that the CDAL 150 evaporates slowly enough, that the reaction between the analyte 80 and the analysis liquid 800 has time to take place, and so the amount of analyte 80 can be determined.

In another embodiment that is similar to FIG. 1A, the CDG 200 injects the CDAL 150 directly along the PDCS axis 402 as described in the patent by Arnold, Hendrie and Bronk (U.S. Pat. No. 5,532,140), which is hereby incorporated by reference, for injecting droplets into a linear quadrupole, and then the gas 120 and particles 124 enter the PDCS 400 at a small angle relative to the PDCS axis 402.

Figure 1B:
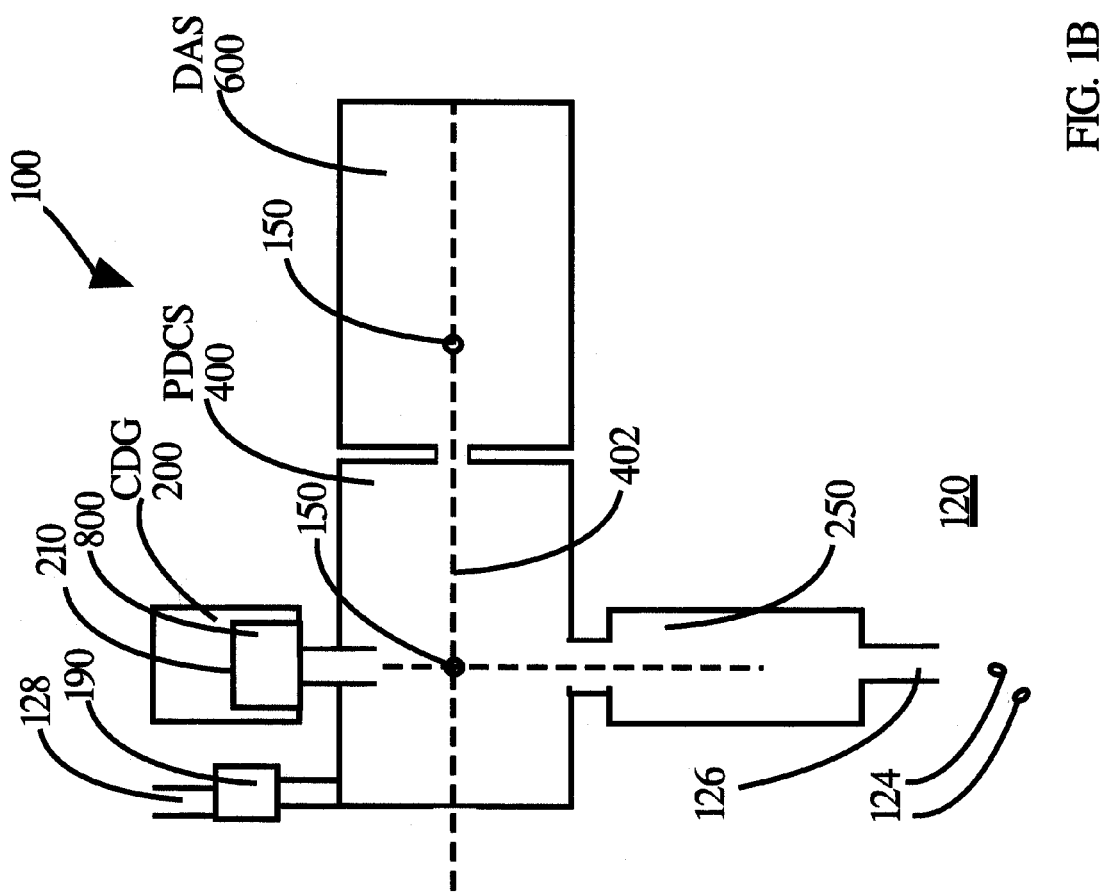

Another exemplar of the APA 100, illustrated schematically in FIG. 1B, differs from the APA 100 shown in FIG. 1A in the arrangement of the CDG 200 and the PDCS 400. In FIG. 1B, the charger 250 is positioned below the PDCS 400, and the flow of the gas 120 is upward. The rate that the pump 190 draws gas 120 from the PDCS 400 is adjusted so that the rate of flow of the gas 120 past the CDAL 150 is approximately that of the settling velocity of the CDAL 150 so that the DC voltage required to levitate the CDAL 150 is relatively small.

Figure 1C:
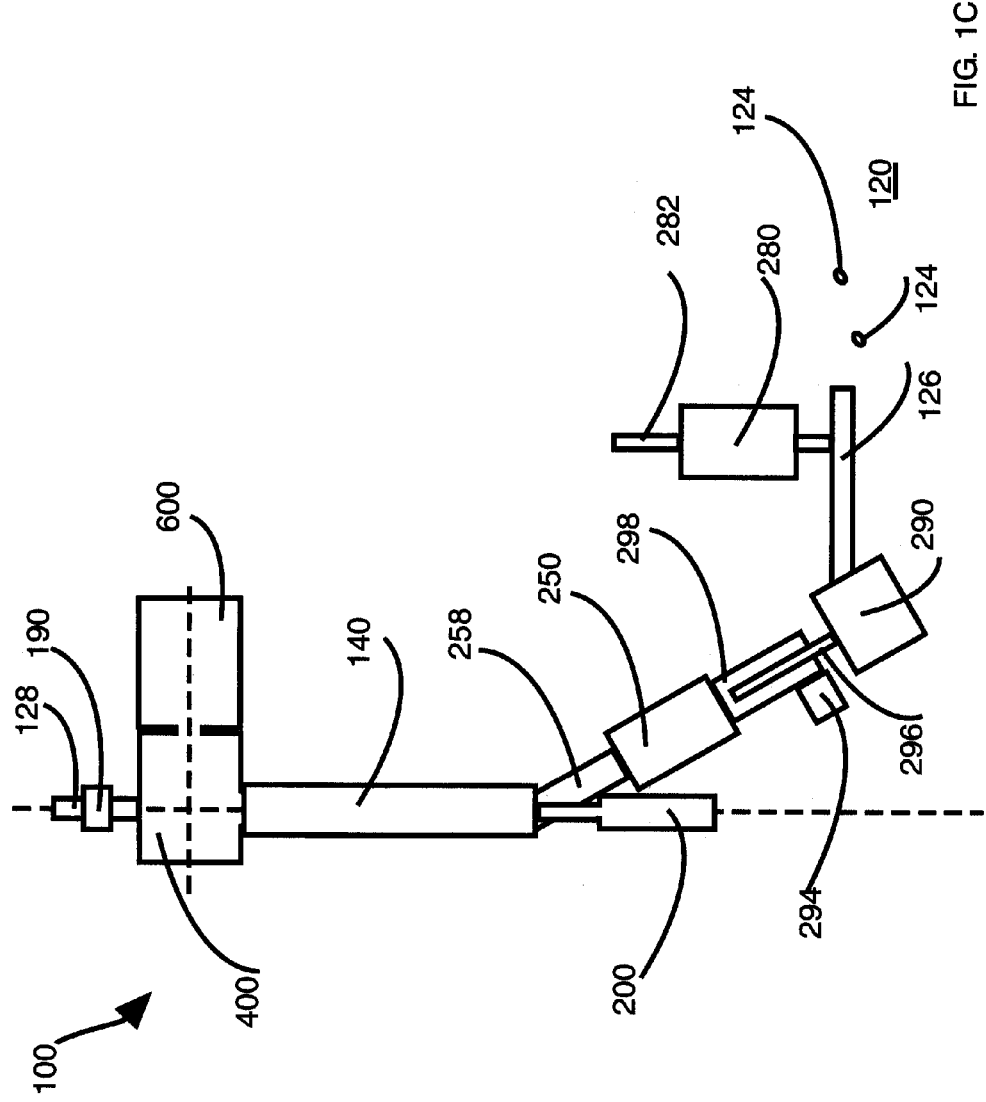

In another exemplar of the APA 100, illustrated schematically in FIG. 1C, a linear-quadrupole-in-an-airtight-container (LQ) 140 connects on the PDCS 400 at the top. The CDG 200 is connected to the bottom of the LQ 140 and injects CDAL 150 into it. The output from the charger 250 is also connected to the bottom of the LQ 140 through tube 258. The pump 190 draws the gas 120 upward through the LQ 140, then through the PDCS 400 and expels the gas 120 and particles that did not combine with CDAL 150 out through the eduction port 128. The flow of the gas 120 upward is sufficiently rapid that the CDAL 150 are pulled upward through the LQ 140 by drag forces with a velocity that is the difference between the settling velocity of the CDAL 150 and the velocity of the flow of the gas 120. The particles are smaller than the CDAL 150 and so flow past the CDAL 150 as it moves upward. Some of the particles 124 flowing past the CDAL 150 combine with it. FIG. 1C also shows an aerosol particle concentrator (APC) 290. The APC 290 concentrates particles 124 in the gas 120 so that lower concentrations of particles 124 that contain analyte 80, as well as particles 124 that contain lower concentrations of analyte 80 can be analyzed. For the APC 290, this exemplar uses the XMX concentrator sold by Dycor, Inc. The gas 120 and particles 124 exit from the APC 290 through a nozzle 296 that is positioned in the center of a sheath-flow tube 298 which provides a means to keep the particles 124 concentrated by the APC 290 from dispersing and so that these particles 124 can be kept near the axis of the LQ 140. The sheath flow enters through a valve 294 that is used to control the sheath flow rate. FIG. 1C also shows a particle counter 280, which is connected to the inlet 126 so that it can sample a part of the gas 120 and particles 124 entering the APC 290. The exhaust from the particle counter 280 exits through the particle counter exhaust port 282. The particle counter 280 measures the number concentration of particles 124, and it estimates the sizes of these particles 124. From this information, once the APA 100 system is calibrated, the volume of the particles 124 that combine with the CDAL 150 to form the CDAL 150 is determined so that the average amount of analyte 80 per volume of the particles 124 that combined with the CDAL 150 can be determined.

The charger 250 imparts a charge to the particles 124 drawn through it. In a preferred embodiment, particles 124 exiting the charger 250 are negatively charged. In one embodiment the charger 250 is of the corona-discharge type as described by R. Vehring, C. L. Aardahl, G. Schweiger and E. J. Davis, "The characterization of fine particles originating from an uncharged aerosol: size dependence and detection limits for Raman analysis," Journal of Aerosol Science, 29, 1045–1061 (1998), especially pp. 1048–1050, and p. 1057, and by C. L. Aardahl, et al., Electrodynamic trapping of aerocolloidal particles: experimental and theoretical trapping limits," Journal of Colloid and Interface Science, 192, 228–237 (1997), both herein incorporated by reference, especially pp. 231–233. In another preferred embodiment, alternating-current corona charging is used to impart more charge per particle 124 with fewer particles 124 lost, as described by M. Lakowski, "Unipolar charging of aerosol particles in alternating electric field," Journal of Electrostatics, 51–52, 225–231 (2001), especially FIG. 2 on page 228 of that paper and the description of the apparatus on p. 227 and 228, both of which are herein incorporated by reference.

Figure 2:
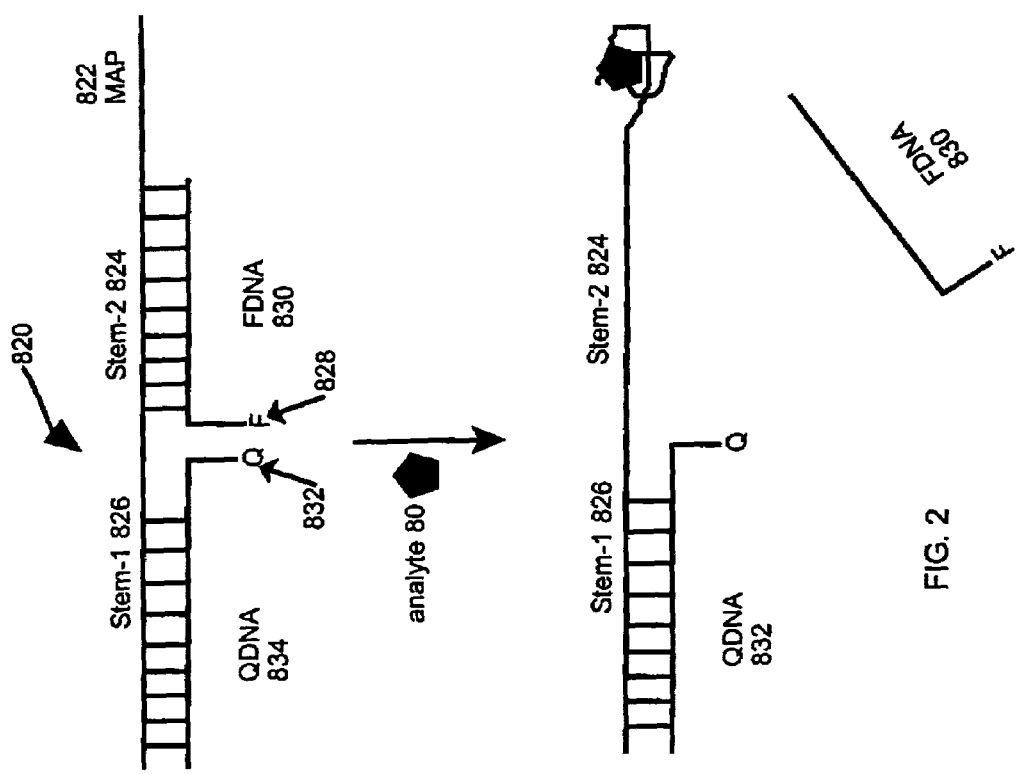

FIG. 2 illustrates schematically one embodiment of the reaction that takes place in the CDAL 150 when analyte 80 is present in the particle 124 that combined with the CDAL 150. FIG. 2 shows how the fluorescence of the analysis liquid 800 changes, so that the fluorescence of the CDAL 150 varies with the amount of analyte 80 in the particles 124 that combined with the CDAL 150. The example shown in FIG. 2 is a variation of that shown in FIG. 6A of an article by R. L. Nutiu and Y. F. Li, "Structure-switching signaling aptamers," Journal of the American Chemical Society, 125, 4771–4778 (2003), (herein incorporated by reference, especially their FIG. 6A. In FIG. 2, the structure-switching signaling aptamer 820 is comprised of: (i) an aptamer (MAP) 822 chosen because it binds selectively to the analyte 80, (ii) a DNA oligonucleotide, Stem-2 824, which is covalently linked to the MAP 822; (iii) a DNA oligonucleotide, Stem-1 826 that is covalently linked to Stem-2 824; (iv) a fluorophore (F) 828; (v) DNA oligonucleotide (FDNA) 830 that is linked to the fluorophore 828; (vi) a quencher (Q) 832; and (vii) a DNA oligonucleotide (QDNA) 834 that is linked to the quencher 832. The FDNA 830 forms the DNA duplex with Stem-2 822. The QDNA 834 forms the DNA duplex with Stem-1. In this structure-switching signaling aptamer 820, the fluorophore 828 and the quencher 832 are held near each other and the quencher 832 quenches the fluorescence of the fluorophore 828, so that the fluorophore 828, fluoresces very weakly if at all. When the analyte 80 is present, the MAP 822 of the structure switching signaling aptamer 820 binds to the analyte 80 as illustrated in FIG. 2, and thereby releases the FDNA 830 so that the fluorophore 828 is no longer quenched, and can fluoresce brightly. The reaction illustrated in FIG. 2 differs from that shown in FIG. 6A of Nutlu and Li, in that the F 828 and Q 832 are interchanged so that the FDNA 830 diffuses relatively rapidly, even in cases where the analyte 80 has a high molecular weight. The FDNA 830 can diffuse throughout the CDAL 150 even if the analyte 80 is a bound to the surface of the particle 124 and the particle 124 is too large to diffuse significantly. This ability of the fluorophore 828 to diffuse relatively rapidly throughout the CDAL 150 is important because otherwise it can be much more difficult to measure the amount of the fluorophore (F) that is unquenched in the CDAL 150 (see e.g., S. C. Hill et al., "Simulation of single-molecule photocount statistics in microdroplets," Analytical Chemistry, 70, 2964–2971 (1998)). For cases where the analyte 80 is an oligonucleotide, the approach illustrated in FIG. 2 is used in one exemplar, but for these analytes 80 the aptamer (MAP) 822 is an oligonucleotide that is complementary to the analyte 80.

Referring again to FIGS. 1A, 1B, and 1C, the charged-droplet generator (CDG) 200 ejects a charged-droplet-of-the-analysis-liquid CDAL 150 when the CCSVES sends it a signal. In one embodiment, the CDG 200 is as described by Arnold et al. (U.S. Pat. No. 5,532,140, column 4). In the preferred embodiment the CDAL 150 is positively charged because the particles 124 in the preferred embodiment are given a negative charge by the charger 100.

FIGS. 3A, 3B, 3C, and 3D illustrate an exemplar of the PDCS 400 that is suitable for the APA 100 illustrated in FIG. 1A. This PDCS 400 includes a linear quadrupole of the PDCS (LQ-PDCS) 410, that is positioned horizontally, to levitate the CDAL 150 and to focus particles 124 near the CDAL 150 so that collisions between CDAL 150 and the particles 124 are more likely. The PDCS 400 also includes an upstream ring 420 and a downstream ring 422 that surround the LQ-PDCS 410, a plate 440, holes 442 in the plate 440 that the gas 120 passes through on its way to the pump 190, and a PDCS-container 450. The PDCS container 450 is substantially airtight except for orifices 448: an entrance orifice 448A, here used to receive particles 124 from the charger 250 and CDAL 150 from the CDG 200, and so in this embodiment the charged-droplet input to the PDCS and the charged-particle input to the PDCS are identical; an PDCS-exit-orifice 448B through which CDAL 150 moves into the DAS 600; and a pump orifice 448C to remove the gas 120 that is drawn through the pipe 446 that connects to the pump 190. The pump 190 draws gas 120 from the PDCS-exit-orifice 448C so that the gas 120 and particles 124 flow around the levitated CDAL 150. The plate 440 has holes such that the gas 120 that is drawn into PDCS 400 and out through the PDCS-exit-orifice 448C flows in a manner that is substantially uniform about the PDCS axis 402, so that the gas 120 does not substantially push the CDAL 150 or particles 124 in a direction perpendicular to the PDCS axis 402. The voltages applied to the LQ-PDCS 410 are similar to those described in Izmialov et al., cited above.

The voltages applied to the rings 420 and 422 are of the same polarity as the CDAL 150, in order to hold the CDAL 150 in the LQ-PDCS 410. When it is time to eject the CDAL 150 from the LQ-PDCS 410, the voltage applied to the downstream ring 422 is removed so that the CDAL 150 is repelled by the charges on the upstream ring 420 toward the DAS 600. Once the CDAL 150 passes the downstream ring 422 as it moves toward the DAS 600, the positive voltage is applied again to the downstream ring 422, in order to further propel the CDAL 150 toward the DAS 600, and also to be ready to hold the next CDAL 150 injected into the PDCS 400.

Figure 3C:
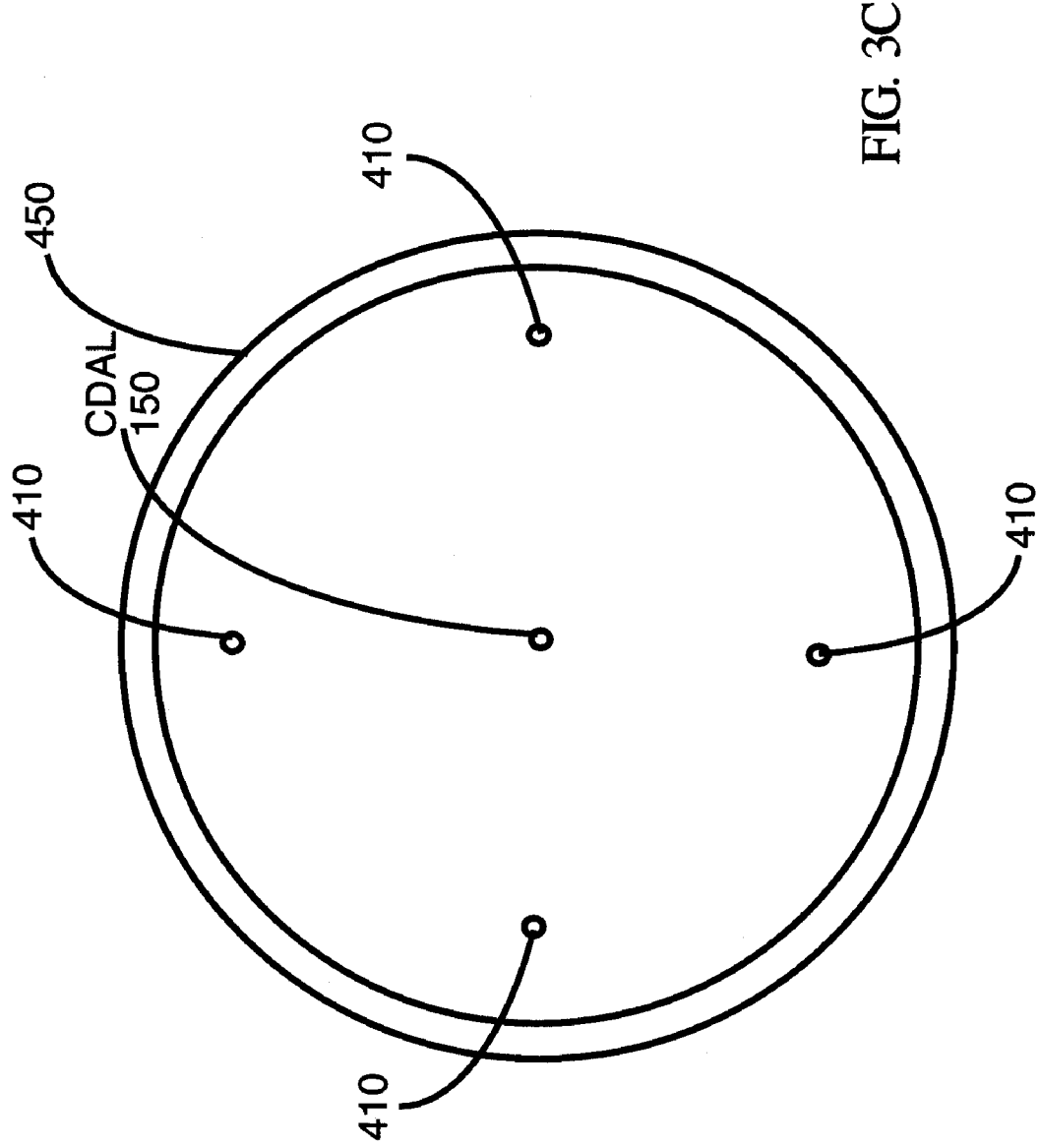
Figure 3E:
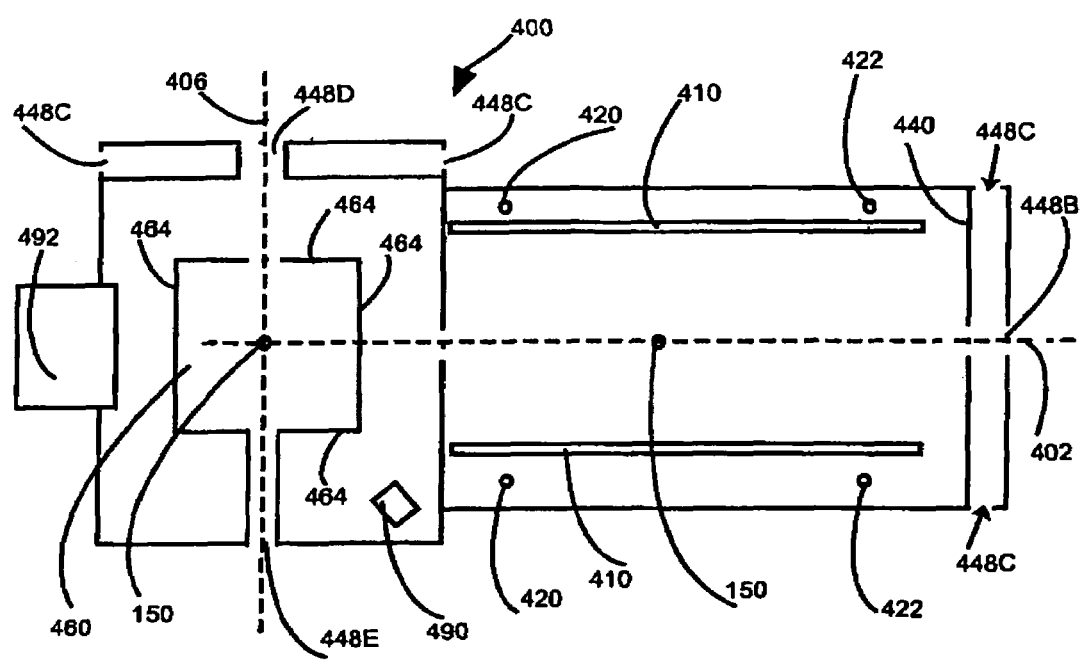
Figure 3F:
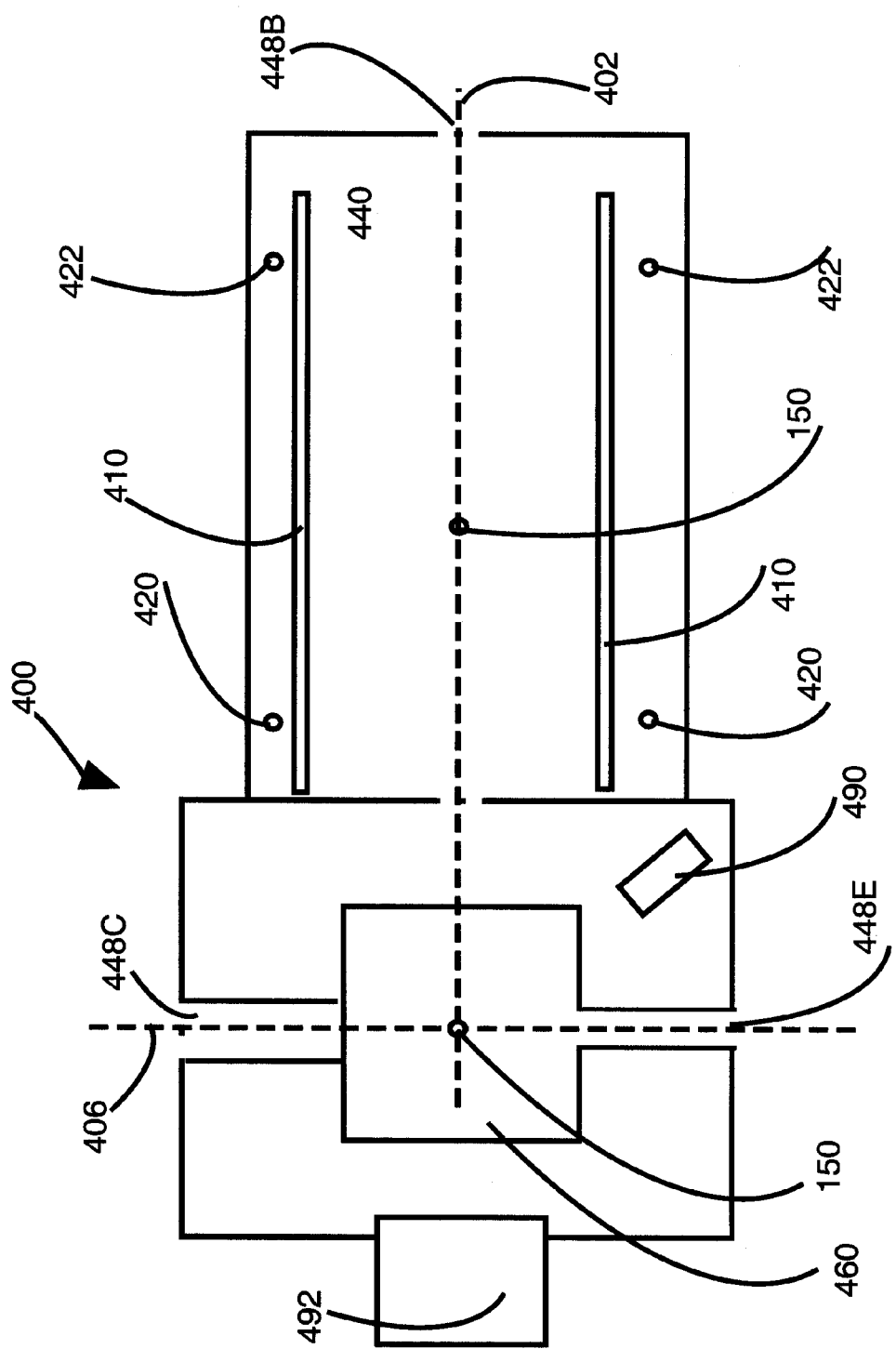

FIG. 3E illustrates another exemplar of the PDCS 400 that is suitable for use with the APA 100 shown in FIG. 1B. In addition to most of the components illustrated in FIG. 3A, this PDCS 400 includes a cubic EDB (CEDB) 464 of the type described by E. E. Allison and B. R. F. Kendall, "Cubic electrodynamic levitation trap with transparent electrodes," Reviews of Scientific instruments, 67, 3806–3812 (1996), especially FIGS. 1 and 2, p. 3807, and the CEDB used by R. A. Shaw, D. Lamb, and A. M. Moyle, "An Electrodynamic Levitation System for Studying Individual Cloud Particles under Upper-Tropospheric Conditions," Journal of Atmospheric and Oceanic Technology, 17, 940–948 (2000), both herein incorporated by reference. In FIG. 3E, the CEDB is aligned so that only one of the six CEDB electrodes 464 is visible. In the work of Kendall et al., and Shaw et al., referenced above, the electrode can take up the whole side of the cube, with only small spacer regions between these electrodes, and small holes can be cut in these electrodes without causing droplets to be levitated substantially less well. In the exemplar illustrated in FIG. 3E, the CDAL 150 is levitated in the CEDB 460 while the gas 120 and particles 124 flow past it so that the CDAL 150 and particles 124 can collide. In FIG. 3E, the CDAL 150 enters through orifice 448D, and the gas 120 and particles 124 enter through 448E. To levitate the CDAL 150 for collisions with the particles 124, the voltages on the OEDB 460 are as described by Shaw et al. (2000) referenced above, that is, alternating current (AC) voltages are applied to those electrodes 464 that are parallel to the vertical direction, shown with a z-axis 406, while only direct current (DC) voltages are applied to the electrodes perpendicular to the z axis 406. Once it is time to eject the CDAL 150, the voltages applied to the CEDB are switched so that the AC voltages are applied to the four electrodes that are parallel to the z axis 406, and DC voltages are applied to the electrodes perpendicular to the z axis so that the CDAL 150 is pushed toward, and then into the LQ-PDCS 410. Then the CDAL 150 is ejected from the LQ-PDCS 410 into the DAS 600 as described above. Levitation of the CDAL 150 while the flow of the gas 120 is upward requires a smaller DC voltage to counter the gravitational force on the CDAL 150, and so the voltages applied to the electrodes 464 are smaller, and so the DC fields that push both the CDAL 150 and the particles 124 are smaller. Also in FIG. 3E is a laser diode 490 to illuminate the CDAL 150 and a video camera 492 to monitor the position of the CDAL 150 so that the voltages applied to the electrodes 464 can be adjusted to stabilize the particle position as described by D. Lamb, A. M. Moyle, and W. H. Brune, "The Environmental Control of individual Aqueous Particles in a Cubic Electrodynamic Levitation System," Aerosol Science and Technology, 24, 263–278 (1996), especially p. 265, herein incorporated by reference. Another exemplar of the PDCS 400 that is suitable for use with the APA 100 shown in FIG. 1C. It does not include the plate 440 of the PDCS shown in FIG. 3E.

Figure 4A:
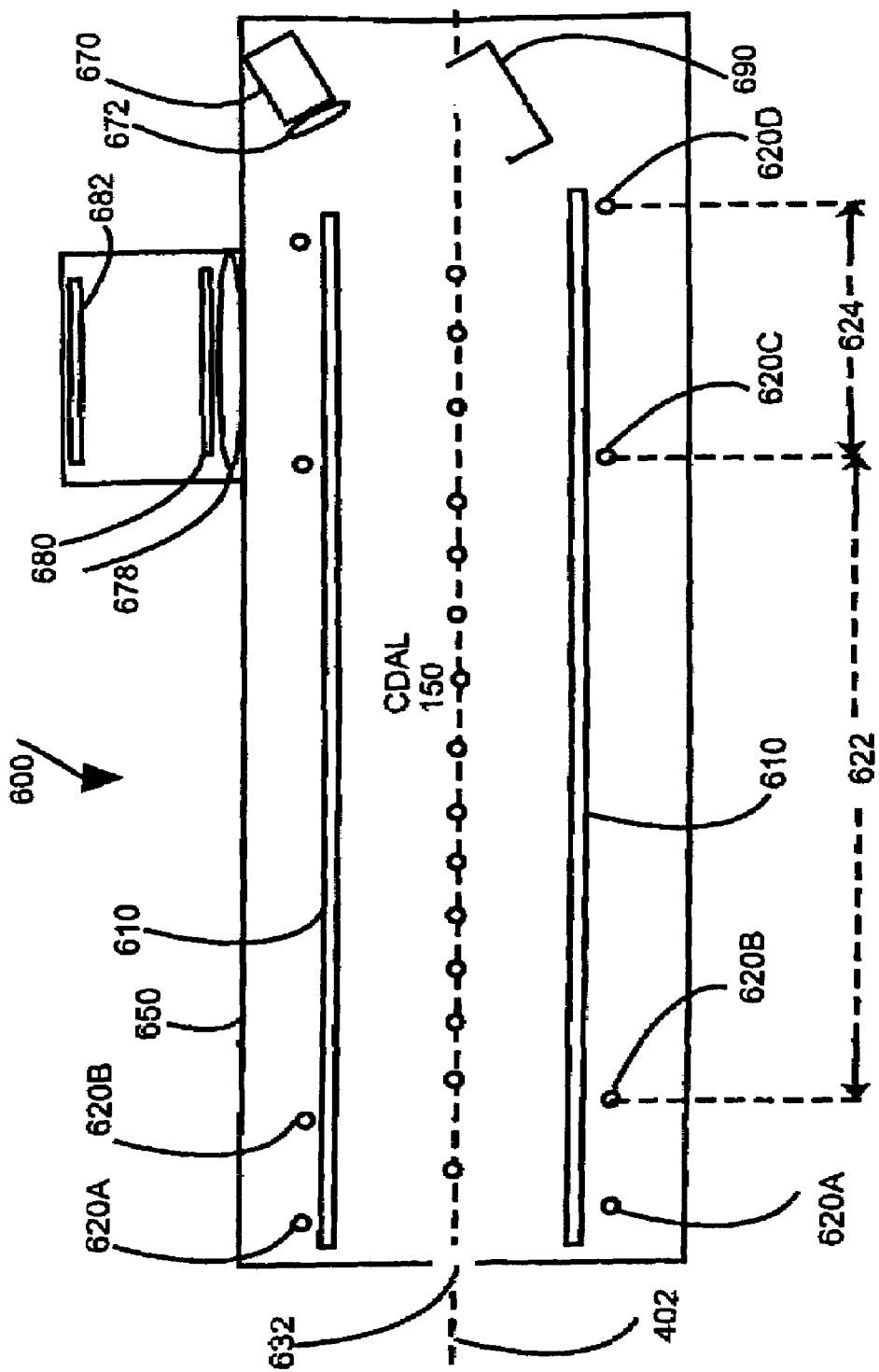

FIG. 4A illustrates schematically one embodiment of the DAS 600. FIG. 4A includes components such as a linear quadrupole of the DAS (LQ-DAS) 610; a multiplicity of DAS rings 620 that surround the LQ-DAS 610; and a DAS container 650. The DAS container 650 is substantially airtight except for a DAS input orifice 632 through which the CDAL 150 moves from the PDCS 400 into the DAS 600. FIG. 4A also includes components such as a laser diode (LD) 670 to excite fluorescence in the CDAL 150, an LD-lens 672 to direct the emission from the LD 670 to at least one CDAL 150; a detector lens 678; a photodetector array 682 to detect the fluorescence; and a detector filter 680 to block the emission from the LD 670 from reaching the photodetector array 682.

Typically, multiple CDAL 150 are levitated between the second DAS ring 620B and the third DAS ring 620C, and these CDAL 150 are separated somewhat uniformly because they are uniformly charged and repulse one another. The holding region 622 is the region between the second DAS ring 620B and the third DAS ring 620C. The fluorescence of the CDAL 150 levitated between the third DAS ring 620C and the fourth DAS ring 620D is measured when the number of CDAL 150 between these DAS rings 620C and 620D is constant. The measurement region 624 is the region between the third and fourth DAS rings 620C and 620D.

In the embodiment described here the CDAL 150 is positively charged. Most of the time the potential applied to the first DSA ring 620A is positive so that CDAL 150 levitated near the axis of the DAS 600 are repulsed if they move toward the inlet. When a CDAL 150 is ejected from the PDCS 400 toward the DAS 600, the voltage of the first DAS ring 620A is lowered briefly so that the CDAL 150 can enter the DAS 600. That CDAL 150 is then held between the first DAS rings 620A and the second DAS ring 620B. Then the voltage of the first DAS ring 620A is raised while the voltage on the second DSA ring 620B is lowered, so that the CDAL 150 is pushed toward the measurement region 624, and the voltages of the third and fourth DAS rings 620C and 620D are also lowered so that the CDAL 150 in the holding region 622 that is nearest the third DAS ring 620C enters the measurement region 624 and the CDAL 150 nearest the fourth DAS ring 620D moves out of the measurement region 624 and into a receptacle 690 where it is held, along with all the other CDAL that enter the receptacle 690 for possible further analysis.

The emission from the laser diode (LD) 670 is focused by the LD-lens 672, so that this emission somewhat uniformly illuminates the CDAL 150 in the measurement region 624 and excites fluorescence in the CDAL 150. The detector filter 680 passes the fluorescence emission from the CDAL 150 and blocks the emission from the LD 670. The fluorescence emission from the CDAL 150 passes through the detector filter 680 and is imaged by the detector lens 678 onto the detector array. The CCVSE reads these fluorescence values from the photodetector array 682. There are as many measurements of the fluorescence of each CDAL 150 as CDAL 150 levitated in the measurement region 624 at any time. These multiple measurements are used to ascertain any time-dependent variations of the fluorescence measured which may occur if the reaction between the analyte 80 and the analysis liquid 800 is not essentially complete by the time the CDAL 150 reaches the measurement region 624, or if the fluorophore 828 has not diffused sufficiently so that the fluorescence of the CDAL 150 varies only little as the CDAL 150 rotates.

Figure 4B:
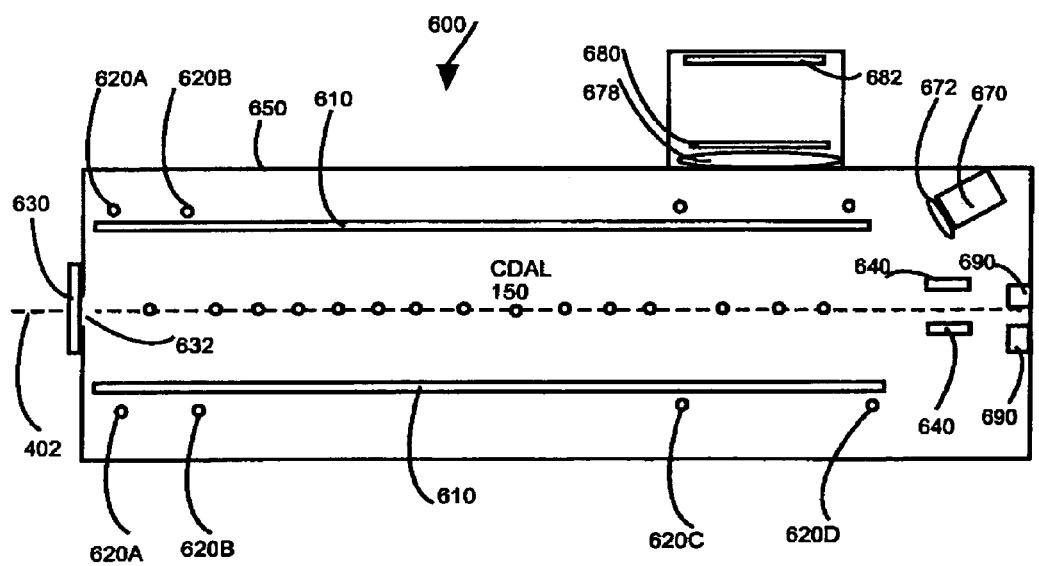

FIG. 4B illustrates schematically another exemplar of the DAS 600. In addition to the components of FIG. 4B, it includes deflection plates 640 and two receptacles 690 so that CDAL 150 ejected from the LQ-DAS 610 can be sorted by applying voltages to the deflection plates 640, in order to sort CDAL 150 having a greater fluorescence from those having a lesser fluorescence. This exemplar of the DAS 600 also includes a shutter 630 in front of the DAS orifice 632. This shutter 630 is closed most of the time, but is opened briefly when a CDAL 150 is ejected from the PDCS 400 into the DAS 600. This shutter helps to maintain the high humidity in the DAS 600. Also shown in FIG. 4B is a water level sensor that senses the level of water in the container, and a water pump that pumps a small amount of water into the bottom of the container when the water level drops below the required level, so as to keep the humidity in the chamber high enough that the evaporation of the CDAL 150 is not rapid.

Another exemplar of the APA 100 is shown in FIG. 5. A vertically oriented linear quadrupole (LQ) 910 is surrounded by an airtight container 920 that is connected below to the charger 250 and CDG 200, and is connected above to a tube 924 that is connected to an impactor 930 which is connected with a pipe 446 to a pump 190. Impactors are discussed, for example, in W. C. Hinds, Aerosol Science and Technology: Properties Behavior and Measurement of Airborne Particles (Wiley, N.Y., 1982), especially pp. 113–124, included herein by reference. The pump 190 lowers the pressure in the tube and the top of the LQ 910 so that the CDAL 150 and particles 124 are drawn upward through the LQ 910 and are focused substantially near the axis of the LQ 910 so that the particles and CDAL 150 tend to combine with each other as they travel upward through the LQ 910 so that the fluorescence of the CDAL 150 can change according to the amount of the analyte 80 in the particles 124. A laser diode 990, a filter 992, a photodetector 994 and lenses 996 are used to measure the fluorescence of the CDAL as it exits the LQ 910 so that the amount of analyte in the particles can be determined. Because this exemplar shown in FIG. 5 has no DAS 600, this exemplar is applicable to combinations of particles 124, analytes 80, and analysis liquids 800 for which the reactions between the particle 24 and the CDAL 150 occur relatively quickly, for example in a case where the analyte 80 is known to occur in particles 124 that are liquid, or in cases where the analyte 124 occurs in a high concentration in the particles 124, and the analyte 80 dissolves especially quickly in the analysis liquid 800, and the required accuracy for the measurement of the amount of analyte 80 is not too high.

Figure 6:
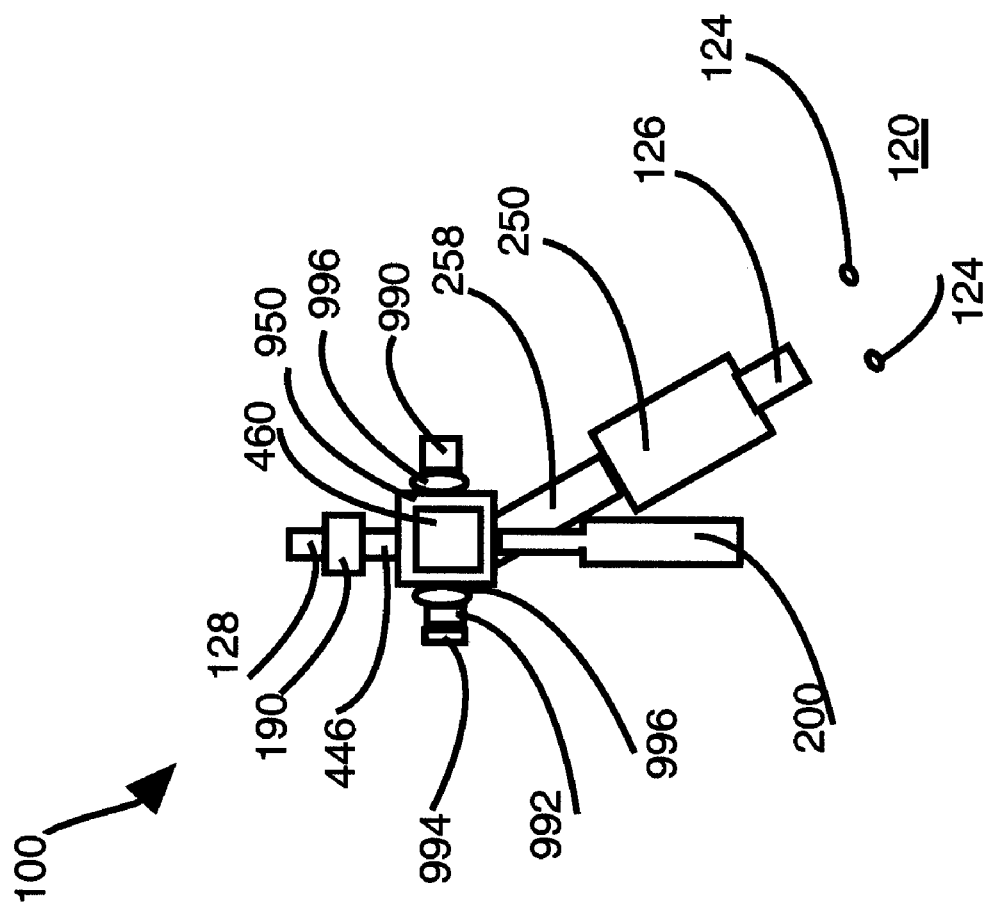

Another exemplar of the APA 100 is shown in FIG. 6. The CDAL 150 is injected from the CDG 200 into a particle-droplet-collision-and-analysis subsystem (PDCAS) 950 where it is levitated by a CEDB 460 and combines with particles 124 that are have been drawn through the charger 250. A laser diode 990, a filter 992, a photodetector 994, and lenses 996 are used to measure the fluorescence of the CDAL 150 as the CDAL 150 is levitated in the PDCAS 950. The APA 100 in FIG. 5 is similar to that illustrated in FIGS. 1B and 1C, with the major difference being that there is no DAS 600 to keep the humidity high in order to reduce the evaporation rate of the CDAL 150. Because there is no DAS 600 in the exemplar shown in FIG. 6, this exemplar is applicable to combinations of particles 124, analytes 80, and analysis liquids 800 for which the reactions between the particle 24 and the CDAL 150 occur relatively quickly, for example in a case where the analyte 80 is known to occur in particles 124 that are liquid, or in cases where the analyte 124 occurs in a high concentration in the particles 124, and the analyte 80 dissolves especially quickly in the analysis liquid 800, and the required accuracy for the measurement of the amount of analyte 80 is not too high.

Although only the measurement of the fluorescence intensity is described here in detail, other fluorescence properties such as the fluorescence polarization, the fluorescence spectrum, and the fluorescence lifetime can also be used in some embodiments of the APA 100, and methods for measuring these properties are well enough known, that more does not need to be stated here. Also, methods for measuring other optical properties such as the light scattering properties of intensity, polarization, spectral intensity, and angular-dependent intensity have been described by many researchers.

Although various preferred embodiments of the present invention have been described herein in detail to provide for complete and clear disclosure, it will be appreciated by those skilled in the art that variations may be made thereto without departing from the spirit of the invention or the scope of the appended claims.

I claim:

1. An aerosol-particle analyzer (APA) for measuring the amount of an analyte in particles in a gas comprising:
   (a) an analysis liquid chosen such that when the analysis liquid is mixed with the particles, an optical property of the analysis liquid varies according to the amount of the analyte in the particles;
   (b) a charged droplet generator, having a charged droplet generator output, that generates a charged droplet of the analysis liquid (CDAL) and ejects it out of said charged-droplet generator output when signaled to do so;
   (c) a charger, enclosed in a gas-tight enclosure, having a gas input and charged particle output, arranged to:
      (i) accept the gas and the particles therein through said gas input;
      (ii) impart an electrical charge to any of said particles accepted, such that the now charged particles will have a charge opposite that of the CDAL; and
      (iii) permit the gas containing the charged particles to exit through the charged particle output;
   (d) a particle-droplet-collision subsystem (PDCS) consisting of an electrodynamic levitator enclosed in a gas-tight container, having a charged-droplet input connected to the charged-droplet generator output, a charged particle input connected via gas-tight connection to the charged particle output, a PDCS CDAL output, and a vacuum connection that:
      (i) accepts the CDAL via the charged-droplet input;
      (ii) accepts the gas containing the charged particles via the charged particle input;
      (iii) levitates the CDAL into a position where the gas containing the charged particles drawn from the charger flows past it so that the charged particles, collide with and combine with the CDAL in part because they are electrically attracted to the oppositely charged CDAL; and
      (iv) ejects the CDAL that has combined with the charged particles, in a desired direction via the PDCS CDAL output;
   (e) a vacuum pump connected to the PDCS vacuum connection that draws the gas and particles into the charger gas input and through the charger and then on into the PDCS, where the gas and any particles not combined with the CDAL are then evacuated;

(f) a droplet analysis subsystem (DAS), having an input orifice for accepting the CDAL that has combined with the charged particles consisting of:

(i) an electrodynamic levitator that levitates the CDAL that has combined with the charged particles ejected by the PDCS and holds them while the reaction between the CDAL and the analyte occurs;

(ii) a means to control the motion of the particles in the electrodynamic levitator;

(iii) a container that surrounds the levitated CDAL and that is substantially airtight, except for the orifice through which the CDAL enter, so that the CDAL does not evaporate quickly, and so that air currents do not push the CDAL out of the electrodynamic levitator;

(iv) a means to detect changes in the optical property of the levitated CDAL, so that the amount of analyte in the CDAL, and in the particles that combined with the CDAL, can be determined from these measurements of the optical property; and (v) a receptacle to collect and store the CDAL after the optical property of the CDAL has been measured.

2. The APA of claim 1 wherein the optical property is a fluorescence property chosen from a group consisting of the fluorescence intensity, the fluorescence polarization, the fluorescence spectrum, and the fluorescence lifetime.

3. The APA of claim 1 wherein the optical property is a light scattering property chosen from a group consisting of the intensity, polarization, spectral intensity, and angular-dependent intensity.

4. The APA of claim 1 wherein the analysis liquid is a water solution that contains sensor molecules that selectively binds to the analyte.

5. The APA of claim 4 wherein the sensor molecule is protein.

6. The APA of claim 4 wherein the sensor molecule is an aptamer.

7. The APA of claim 4 wherein the sensor molecule is phage-displayed epitope.

8. The APA of claim 4 wherein the sensor molecule is a nucleic acid.

9. The APA of claim 1 wherein the charger generates a corona discharge.

10. The APA of claim 1 wherein the charger is of the alternating-current corona charging type.

11. The APA of claim 1 wherein the electrodynamic levitator of the PDCS is a linear quadupole with a means to control the positions of particles held within the linear quadrupole.

12. The APA of claim 1 wherein the electrodynamic levitator of the PDCS is a cubic electrodynamic balance.

13. The APA of claim 12, wherein the PDCS further includes a linear quadrupole positioned between the cubic electrodynamic balance and the DAS, and surrounded by at least two rings, so that it can inject the CDAL into the DAS that has a particularly small orifice.

14. The APA of claim 1, wherein the charged-droplet input of the PDCS and the charged particle input of the PDCS are identical, because the charged-droplet generator output and the charged particle output of the charger are connected via a gas-tight connection before connecting to the PDCS.

15. The APA of claim 1 wherein the electrodynamic levitator of the DAS is a linear quadrupole.

16. The APA of claim 1 wherein said DAS further includes a shutter that is open when the CDAL is injected into the DAS, and is closed otherwise, so that the rate that water vapor leaves the DAS through the orifice is reduced, so that the humidity in the DAS remains high.

17. The APA of claim 1 wherein said DAS futher includes a means to sort the CDAL into different receptacles according to the measured value of the optical property.

18. The APA of claim 12 further including a vertically positioned linear quadrupole, and a substantially airtight tube that surrounds the vertically positioned linear quadrupole and connects to the charged-particle output of the charger and to the CDAL-output of the charged-droplet generator (CDG), and to the input to the PDCS, so that the CDAL and the particles can combine as they are drawn upward through this linear quadrupole and move upward toward the PDCS.

19. The APA of claim 11 further including: (i) a vertically positioned linear quadrupole that is bent gradually at the upper end so that at the top of this bent linear quadrupole the particles move almost horizontally, so that the electrodynamic levitator of the PDCS can be a linear quadrupole; and (ii) a substantially airtight tube that surrounds the vertically positioned bent linear quadrupole and connects to the charged-particle output of the charger and to the CDAL-output of the charged-droplet generator (CDG), and to the input to the PDCS, so that the CDAL and the particles can combine as they are drawn upward through this bent linear quadrupole and move upward toward the PDCS.

20. The APA of claim 1 further including an aerosol particle concentrator connected to the charger which concentrates the particles before they enter the charger so that the APA is sensitive to particles which contain lower concentrations of analyte and to lower concentrations of particles that contain the analyte.

21. The APA of claim 20 further including a nozzle connected to the output of the aerosol particle concentrator, where said nozzle is positioned inside a sheath-flow tube so that the particles concentrated by the aerosol particle concentrator are kept from dispersing so that a higher fraction of these particles flow past the CDAL so that they can be attracted to the CDAL and combine with it.

22. The APA of claim 1 further including an aerosol particle counter to measure the concentration of, and sizes of, particles in the gas so that the numbers and sizes of particles that combine with the CDAL can be determined approximately by using calibration data.

23. The APA of claim 1 wherein the analysis liquid further contains an additional sensor molecule that selectively binds to an additional region of the analyte.

24. The APA of claim 23 wherein when the additional sensor molecule binds to the additional region of the analyte, the fluorescence of an additional fluorophore changes, and wherein the spectral peak of the fluorescence emission that changes when the sensor molecule binds to the analyte is different from the spectral peak of the fluorescence emission that changes when the additional sensor molecule binds to the additional region of the analyte.

25. The APA of claim 1 wherein the analysis liquid further contains an additional sensor molecule that selectively binds to an additional analyte.

26. The APA of claim 25 wherein, when the additional sensor molecule binds to the additional analyte, the fluorescence of an additional fluorophore changes, and wherein the spectral peak of the fluorescence emission that changes when the sensor molecule binds to the analyte is different from the spectral peak of the fluorescence emission that changes when the additional sensor molecule binds to the additional analyte.

27. The APA of claim 1 wherein said DAS further includes a means to measure multiple optical properties of one CDAL.

28. The APA of claim 1 wherein said DAS further includes a means to open the container and remove and replace the receptacle, so that the CDAL, or what remains from the CDAL after the water has evaporated, can be further analyzed.

29. The APA of claim 1 wherein said DAS further includes a region in the container to hold water that can evaporate to keep the humidity in the DAS high.

30. The APA of claim 29 wherein said DAS further includes a means to detect the water level in the region in the container that holds the water, and a means to inject water into the region in the container that holds the water if this water level drops below some level.

* * * * *